United States Patent [19]

Takaishi

[11] Patent Number: 4,495,940

[45] Date of Patent: Jan. 29, 1985

[54] MASSAGER

[76] Inventor: Hiroshi Takaishi, 73-2, Uchikaburaki-machi, Sakura-shi, Chiba-ken, Japan

[21] Appl. No.: 386,654

[22] Filed: Jun. 9, 1982

[51] Int. Cl.$^3$ .............................................. A61N 23/00

[52] U.S. Cl. .......................................... 128/55; 54/48

[58] Field of Search ........................ 128/48, 49, 52, 55, 128/54, 51; 81/463; 145/29 A, 29 B, 36

[56] References Cited

U.S. PATENT DOCUMENTS

| | | | |
|---|---|---|---|
| 1,543,847 | 6/1925 | Heidbrink | 128/52 |
| 2,234,102 | 3/1941 | Andres | 128/52 |
| 2,626,598 | 1/1953 | Tarwater | 81/463 |
| 3,011,480 | 12/1961 | Vilmerding | 81/463 |
| 3,228,392 | 1/1966 | Speyer | 128/55 |
| 3,837,335 | 9/1974 | Teranishi | 128/52 |

FOREIGN PATENT DOCUMENTS

| | | | |
|---|---|---|---|
| 414667 | 6/1925 | Fed. Rep. of Germany | 128/54 |
| 850080 | 7/1981 | U.S.S.R. | 128/55 |

*Primary Examiner*—Richard J. Apley
*Assistant Examiner*—Harry Macey
*Attorney, Agent, or Firm*—J. Gibson Semmes

[57] ABSTRACT

This massager utilizes percussion waves produced by a powerful hand-held or stationary drive, such as an electric hammer, magnetic hammer or pneumatic hammer, for massaging human bodies. The massager includes an intermediate idler connected to an oscillator rod operated by a drive unit and a hitting pad connected to the intermediate idler. A lower end of the oscillator rod slides freely inside an upper axial cavity in the upper part of the intermediate idler. A lower part of the intermediate idler is linked to a hitting pad through a control spring. This control spring creates a gap for vibration between the lower end of the intermediate idler and the hitting pad.

2 Claims, 4 Drawing Figures

MASSAGER

BACKGROUND OF THE INVENTION

Field of the Invention

This invention relates to a massager that utilizes penetrating percussion waves produced by a hand-held or stationary powerful drive unit as massage waves.

SUMMARY OF THE INVENTION

The causes of physical fatigue accumulate because of the mental and/or physical stress of living in a multifarious society; a substantial number of people complain of various ailments, such as headache, stiff shoulder, lumbago, muscular pain and neuralgia. For instance, persons engaged in agriculture often have stiffness in the lumbar region because they frequently have to stoop during work, and athletes who participate in sports that require sophisticated techniques often have the motor nerve disorders, resulting in supervension such as sprained joints. In general, workers who repeatedly perform the same tasks often strain particular regions, causing tissues to age and decreased locomotion. If people with such problems consult physicians, no diseases are found, but they nevertheless feel pain or weariness and are mentally tired, leading them to plod through days without any will to work.

In order to overcome physical disorders which are not caused by disease, it is necessary to improve physical strength and to develop resistance to such afflictions. However, it is insufficient to seek the remedy of exercise and nutrition. The human body naturally possesses healing power to combat disease and other affliction, and as long as the brain's instructions are properly transmitted to various parts of the body, health is usually maintained. Massage works to accelerate hematogenic activity and thereby invigorate cellular tissues and to facilitate transmission from the brain. The present invention was developed on the basis of the basic principles of massage, and is constructed so that it can be easily used not only by professional massagers and sports trainers but also by ordinary people.

The present invention produces massage waves by transmitting vibration generated by a drive unit in the oscillator directly to a heavy intermediate idler made of a metal such as iron. These percussion waves are then transmitted to a hitting pad connected under the intermediate idler through a strong control spring. Another feature of the present invention is that it can be used easily not only by professional massagists but also by ordinary people to produce penetrating massage waves with a hand-held or stationary drive unit.

The above description and other aspects and novel features of the present invention will emerge more fully in the following detailed description and accompanying drawings. It is to be expressly understood, however, that the drawings are for purpose of illustration only and are not intended to define the limits of the invention.

BRIEF DESCRIPTION OF THE DRAWINGS

The accompanying drawings illustrate the mechanical elements of this unique massager.

DETAILED DESCRIPTION OF THE PREFERRED EMBODIMENTS

Figure 1:
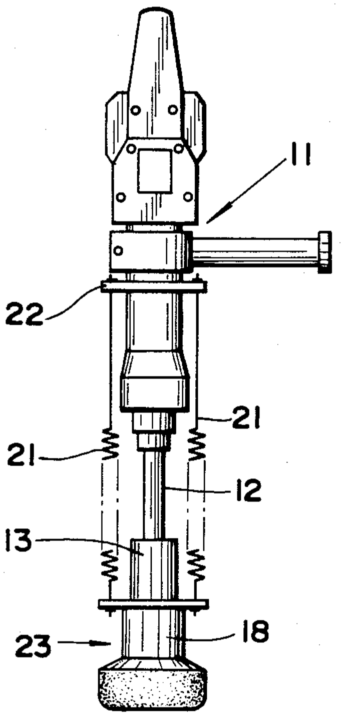
FIG. 1 is a front view of the massager of the present invention.
Figure 2:
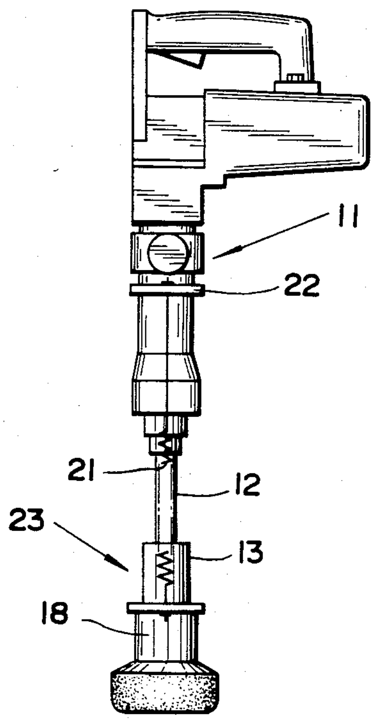
FIG. 2 is a side view thereof.
Figure 3:
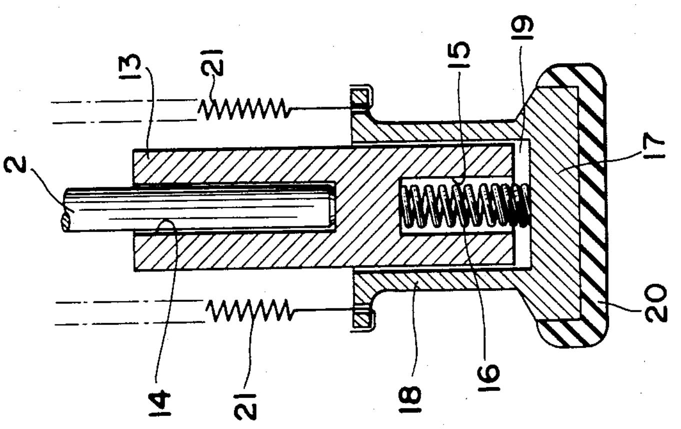
FIG. 3 depicts in fragment an enlarged vertical section showing the details of the parts that generate percussion waves.

The elements of the present invention shown in FIGS. 1 through 3 will be described first. This massager is roughly divided into a drive unit and a percussion wave generator. The drive unit 11 has a motor and a crank built-in, well-known devices for converting the motor's rotary motion into a reciprocating motion in the desired direction by means of the crank and for transmitting this reciprocating motion to the oscillator 12. The lower part of the oscillator 12 is loosely fitted in the upper axial cavity 14 on the upper part of the intermediate tubular idler 13, preferably along its axis. Repetition of the reciprocating motion at a constant frequency in the oscillator 12 transmits percussion waves to the idler 13. It is best to fabricate oscillator 12 and intermediate idler 13 out of impact-and-heat-resistant steel in order to prevent damage and heat resulting from impact and friction. The intermediate idler 13 has a lower axial cavity 15 within its lower portion, opening downwards along its axis. Control spring 16, which requires a compressive force of approximately 80 kg to compress 1 cm of its length, is contained in the a lower axial cavity 15, the lower part of the spring 16 projecting out of the cavity 15. Hitting pad 17 has operative connection with the lower part of the spring.

The hitting pad 17 has a tubular exterior 18 on top, in which the lower part of the intermediate idler 13 can be inserted. The reciprocating motion of the intermediate idler 13 is absorbed by the hitting pad 17. Control spring 16 creates a gap 19 for vibration between the lower end of the intermediate idler 13 and the hitting pad 17 through the upward force of the control spring's contact with the bottom of the tubular part 18. The intermediate idler's 13 reciprocating motion is absorbed by the control spring 16, transmitting only percussion waves generated by metal hitting against metal to the hitting pad 17 through the control spring 16. The virtually flat bottom of the hitting pad 17 is covered with a protector 20, made from a relatively hard rubber or plastic material. The hitting pad 17 is connected to two or more hanging springs 21 hung from the stationary plate 22 of the drive unit 11 with a sufficient elasticity in order to link the whole percussion wave generator 23 with the drive unit 11. The compression strength of the springs 21 can be freely adjusted, and with the drive unit's 11 output adjustment, e.g., a variable resistor, not shown—the output of percussion waves can be adjusted as desired in order to apply finely controlled percussion waves to patients' bodies.

This unit is constructed so that it can be held by the user, and is operated by pressing an area of a patient's body with the lower surface of the hitting pad 17 in order to transmit percussion waves to the patient. A sports trainer or masseur can easily treat athletes or manual laborers to relieve fatigue, reactivate bodily functions and adjust physical balance with this massager.

Figure 4:
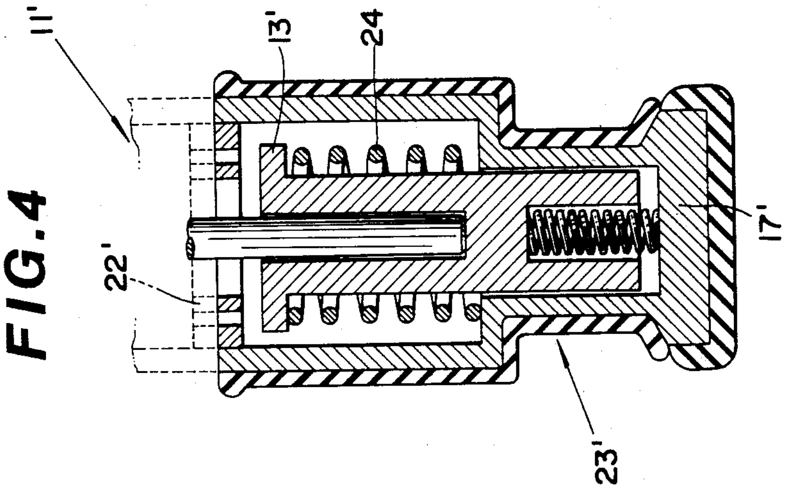
FIG. 4 is a fragmentary view of an enlarged vertical section showing a modified example of the parts that generate percussion waves.

FIG. 4 shows modified percussion wave generator 23' with the hitting pad 17' directly attached to the drive unit's 11' stationary plate 22'.

It is obviously possible to use a wide range of permutations of this massager without subverting its purpose and claims; this massager is not limited to the particular modes of application defined and/or suggested above.

What is claimed is:

1. A massager comprising:

(A) a variable frequency oscillatory motion drive unit;

(B) an oscillator rod with upper and lower ends; the upper end connected to said drive unit;

(C) an intermediate idler with upper and lower parts and upper and lower axial cavities; the lower end of said oscillator rod fitting fully into and sliding freely within the upper axial cavity of the intermediate idler;

(D) a control spring fitting into the lower axial cavity of said intermediate idler;

(E) a hitting pad with an upper tubular portion; said lower part of said intermediate idler fitting into and sliding freely within the upper tubular portion of the hitting pad; said control spring defining a gap between the hitting pad and said intermediate idler for vibration.

2. A massager as claimed in claim 1 further comprising a buffer spring which is interposed between said intermediate idler and said hitting pad; said upper part of the intermediate idler defining a flange, the flange of the idler and said upper tubular portion of the hitting pad confining the buffer spring; the hitting pad is rigidly attached to the drive unit.

* * * * *